US012806042B2

(12) United States Patent
Garrison

(10) Patent No.: US 12,806,042 B2
(45) Date of Patent: Nov. 24, 2026

(54) UPPER EXTREMITY PROSTHESIS

(71) Applicant: NEW YORK SOCIETY FOR THE RELIEF OF THE RUPTURED AND CRIPPLED, MAINTAINING THE HOSPITAL FOR SPECIAL SURGERY, New York, NY (US)

(72) Inventor: Glenn Garrison, Englewood, NJ (US)

(73) Assignee: NEW YORK SOCIETY FOR THE RELIEF OF THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 1064 days.

(21) Appl. No.: 17/910,712

(22) PCT Filed: Apr. 7, 2021

(86) PCT No.: PCT/US2021/026200
§ 371 (c)(1),
(2) Date: Sep. 9, 2022

(87) PCT Pub. No.: WO2021/207373
PCT Pub. Date: Oct. 14, 2021

(65) Prior Publication Data

US 2023/0021372 A1 Jan. 26, 2023

Related U.S. Application Data

(60) Provisional application No. 63/007,053, filed on Apr. 8, 2020.

(51) Int. Cl.
*A61F 2/70* (2006.01)
*A61F 2/54* (2006.01)
(Continued)

(52) U.S. Cl.
CPC ................ *A61F 2/585* (2013.01); *A61F 2/70* (2013.01); *A61F 2/78* (2013.01);
(Continued)

(58) Field of Classification Search
CPC .... A61F 2/50; A61F 2002/5001; A61F 2/585; A61F 2/70; A61F 2/78; A61F 2002/543;
(Continued)

(56) References Cited

U.S. PATENT DOCUMENTS 6,361,570 B1 3/2002 Gow
9,956,093 B1 * 5/2018 Harris ...................... A61F 2/76
(Continued)

FOREIGN PATENT DOCUMENTS

WO 2012055401 A1 5/2012
WO 2017182451 A1 10/2017
(Continued)

OTHER PUBLICATIONS

International Search Report and Written Opinion in PCT Application No. PCT/US2021/026200, mailed Aug. 25, 2021 (11 pages).
(Continued)

*Primary Examiner* — Bruce E Snow
(74) *Attorney, Agent, or Firm* — Leason Ellis LLP

(57) ABSTRACT

An upper extremity prosthesis for placement on a residual limb of a person that includes an elongated member having a first end and an opposite second end and also includes an outer prosthetic shell having a first end and an opposite second end. The prosthesis also includes at least a first support and a second support, wherein the first support and the second support surround and are fixedly coupled to the elongated member at first and second attachment points, respectively. The outer prosthetic shell thus surrounds and is coupled to the first support and the second support. The first
(Continued)

support and the second support can be a disk-shaped structure through which the elongated member passes.

14 Claims, 14 Drawing Sheets

(51) Int. Cl.
*A61F 2/58* (2006.01)
*A61F 2/78* (2006.01)

(52) U.S. Cl.
CPC ... *A61F 2002/543* (2013.01); *A61F 2002/701* (2013.01); *A61F 2002/7887* (2013.01)

(58) Field of Classification Search
CPC ........ A61F 2002/701; A61F 2002/7887; A61F 2/2814; A61F 2002/702; A61F 2/54
See application file for complete search history.

(56) References Cited

U.S. PATENT DOCUMENTS

| | | | | |
|---|---|---|---|---|
| 2009/0093891 | A1 | 4/2009 | Summit | |
| 2014/0081422 | A1 | 3/2014 | Hugate | |
| 2018/0161179 | A1 * | 6/2018 | Sevier | A61F 2/50 |
| 2019/0374354 | A1 | 12/2019 | Hugate | |

FOREIGN PATENT DOCUMENTS

| | | | |
|---|---|---|---|
| WO | 2018064725 | A1 | 4/2018 |
| WO | 2019209980 | A1 | 10/2019 |

OTHER PUBLICATIONS

Extended European Search Report in EP Application No. 21783976.0-1122/4132429, mailed Mar. 18, 2024 (8 pages).

* cited by examiner

UPPER EXTREMITY PROSTHESIS

CROSS REFERENCE TO RELATED APPLICATION

The present application is a U.S. National Phase Application under 35 U.S.C. § 371 of International Patent Application No. PCT/US2021/026200, filed on Apr. 7, 2021, which is based on and claims priority to U.S. Provisional Patent Application No. 63/007,053, filed Apr. 8, 2020, which is directed to an upper extremity prosthesis all of which are incorporated by reference, as if expressly set forth in their respective entireties herein.

TECHNICAL FIELD

The present disclosure is directed to an upper extremity prosthesis and more particularly, to an upper extremity prosthesis for use in below the elbow amputations with an osseointegration post, especially those with short residual limb lengths below the elbow.

BACKGROUND

Amputations are often classified as being either upper extremity amputations or lower extremity amputations.

There are many levels of upper extremity amputations, and with each one comes a different method of rehabilitation as well as a different type of prosthesis. For example, different levels of upper extremity amputations includes but are not limited to: (1) fingers or partial hand (transcarpal); (2) at the wrist (wrist disarticulation); (3) below the elbow (transradial); (4) at the elbow (elbow disarticulation); (5) above the elbow (transhumeral); (6) at the shoulder (shoulder disarticulation); and (7) above the shoulder (forequarter).

Similarly, there are many levels of lower extremity amputations, and with each one comes a different method of rehabilitation as well as a different type of prosthesis. For example, different levels of lower extremity amputations includes but are not limited to: (1) foot, including toes or partial foot; (2) at the ankle (ankle disarticulation); (3) below the knee (transtibial); (4) at the knee (knee disarticulation); (5) above the knee (transfemoral); and (6) at the hip (hip disarticulation.

A below elbow arm prosthetic is thus one which is located below the elbow and above the hand and is used after an upper extremity amputation is performed. An upper extremity amputation can result due to any number of conditions, including, but not limited to, severe trauma, blood vessel disorder (atherosclerosis), diabetes mellitus, malignancy, infection, congenital amputation, and gangrene. A below elbow (BE) or transradial prosthesis is custom made for a person who has had a BE or transradial amputation. The prosthesis generally consists of a custom-made socket, optional liner, wrist unit, and terminal device (e.g., a hand). Sometimes, the prosthesis can consist of a sleeve or other harness, depending on the suspension system used for that patient.

Osseointegration

Osseointegration is a blossoming field in the surgical space and generally, osseointegration is the scientific term for bone ingrowth into a metal implant. An artificial implant is permanently, surgically anchored and integrated onto bone, which then grows into the implant. Osseointegration is most commonly used in dental implants. It has been very successful in these uses for decades. Osseointegration limb replacement is a type of surgery in which a limb prosthesis is connected directly to the skeleton.

When dealing with below elbow amputations, the length of the residual limb may cause complications in terms of upper extremity prosthetic fitting, etc. The present disclosure is directed to overcoming this challenge and provide an improved solution for mounting a prosthetic limb for a below the elbow amputee.

BRIEF DESCRIPTION OF THE DRAWING FIGURES

DETAILED DESCRIPTION OF CERTAIN EMBODIMENTS

Figure 1:
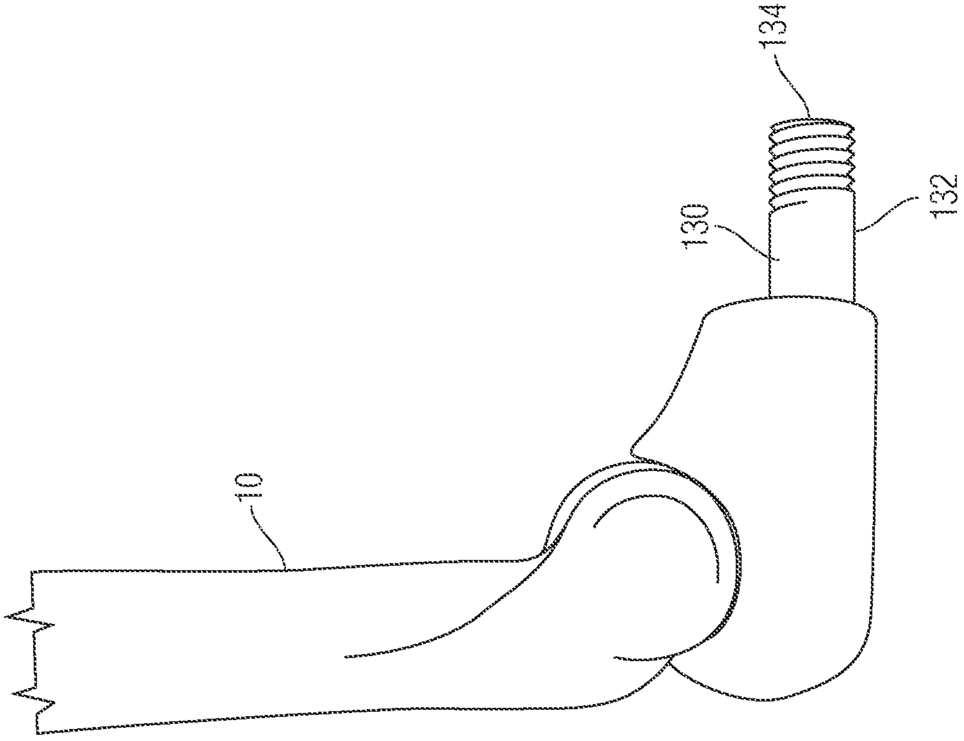
FIG. 1 is a side elevation view of a residual limb with an osseointegration dual taper post being attached thereto.
Figure 3:
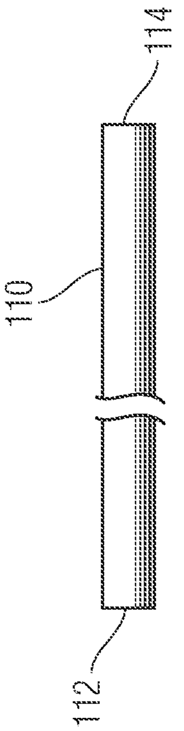
FIG. 3 is a side elevation view of an elongated member for detachable connection to the first connector.
Figure 2:
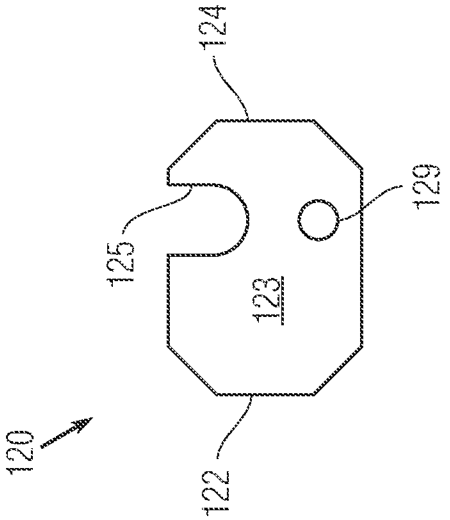
FIG. 2 is a side elevation view of a first connector.
Figure 4:
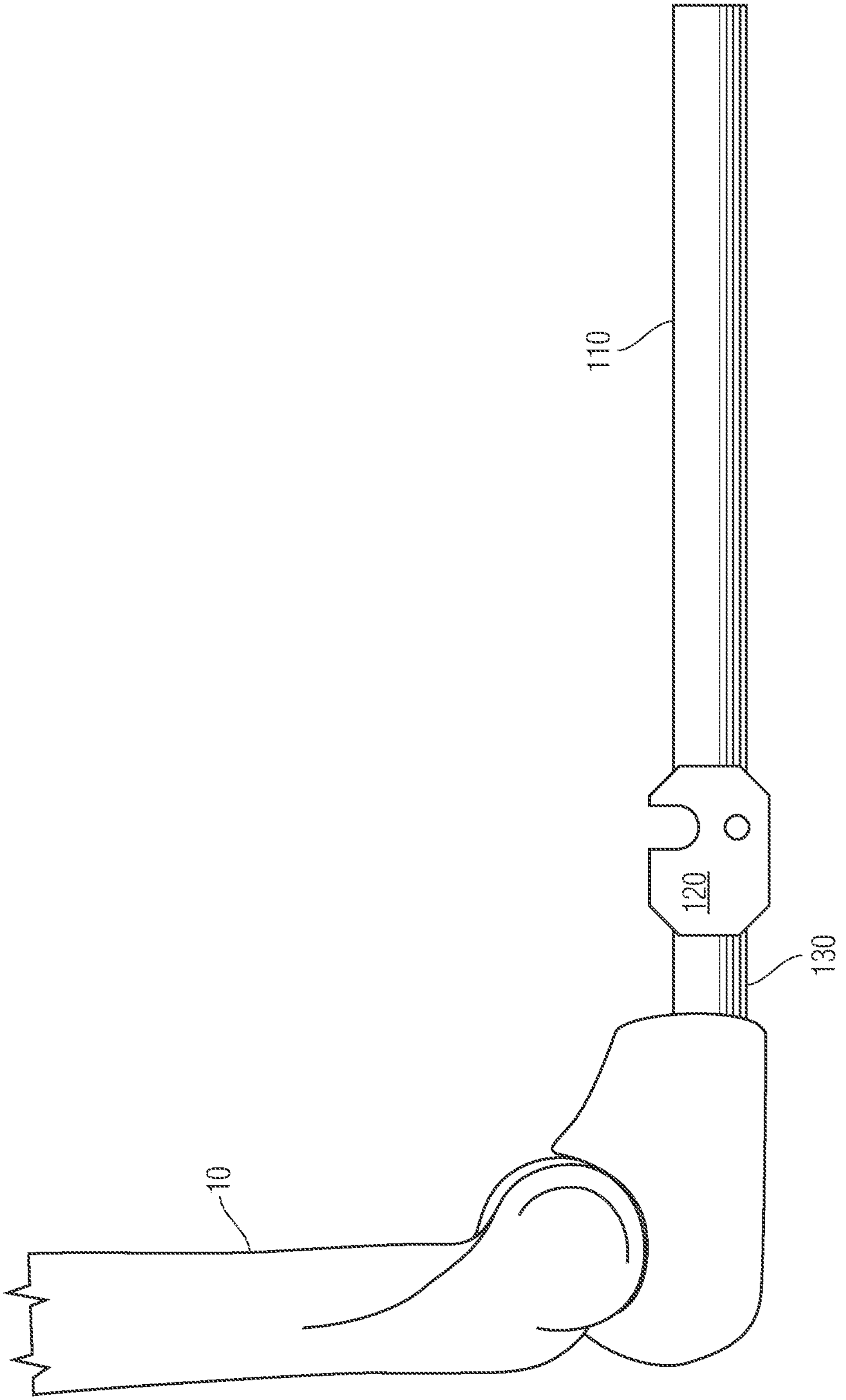
FIG. 4 is a side elevation of the assembled internal components for attachment to the residual limb including the first connector and the elongated member.
Figure 5B:
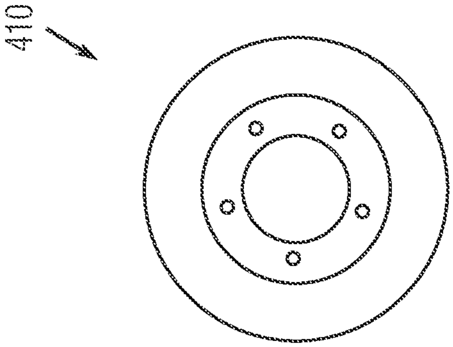
FIG. 5B is an end view of the wrist unit.
Figure 5A:
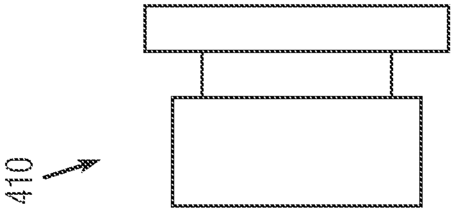
FIG. 5A is a side elevation view of wrist unit.
Figure 6C:
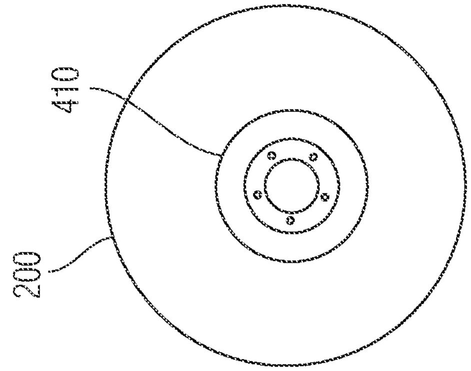
FIG. 6C is a second end view of the shell.
Figure 6A:
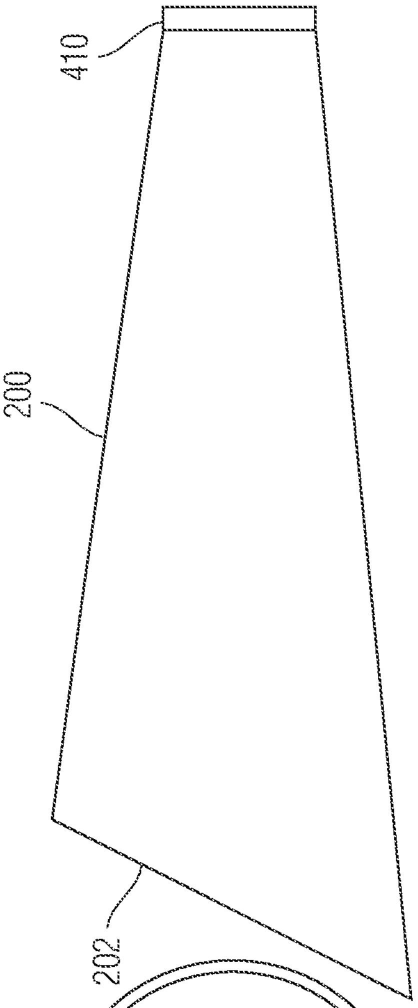
FIG. 6A is a side elevation view of an outer prosthetic shell.
Figure 6B:
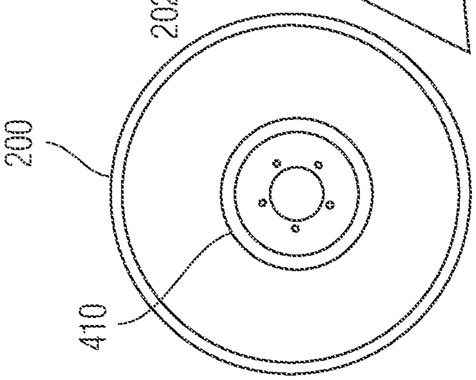
FIG. 6B is a first end view of the shell.
Figure 7:
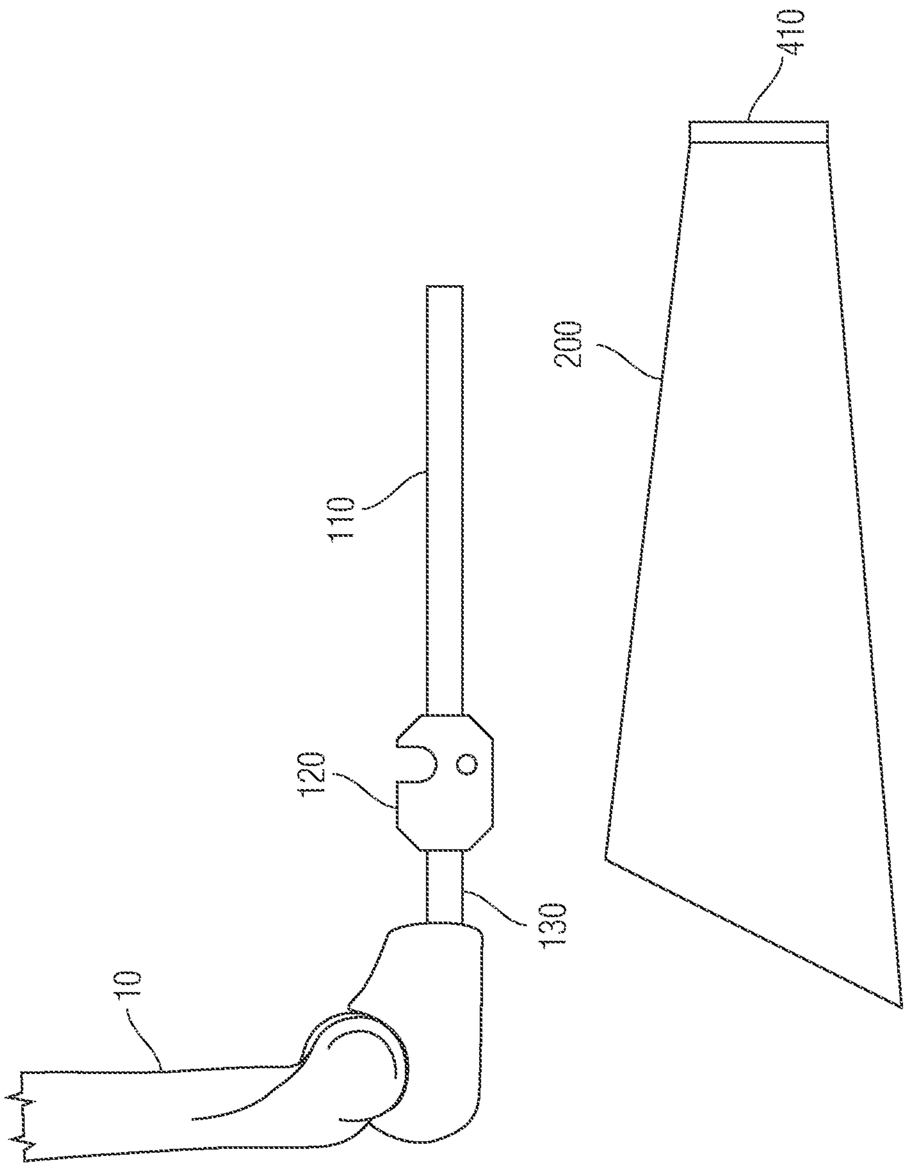
FIG. 7 is an exploded side elevation view of the assembled inner components attached to the residual limb and the outer prosthetic shell being exploded therefrom.
Figure 8A:
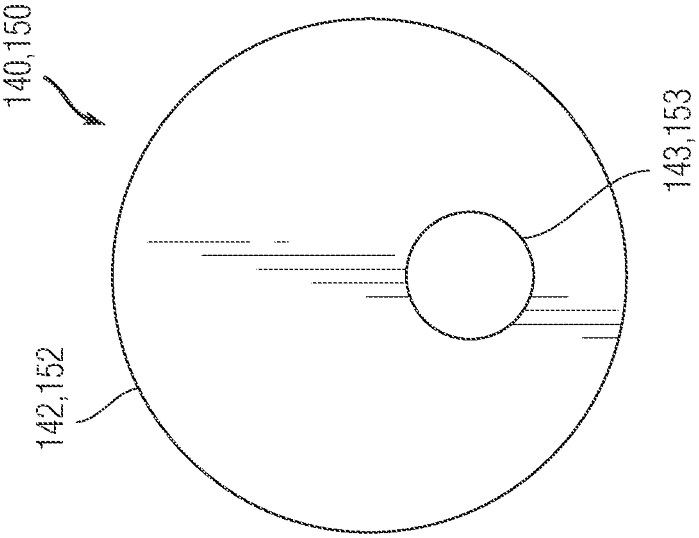
FIG. 8A is an end view of an exemplary inner support.
Figure 8B:
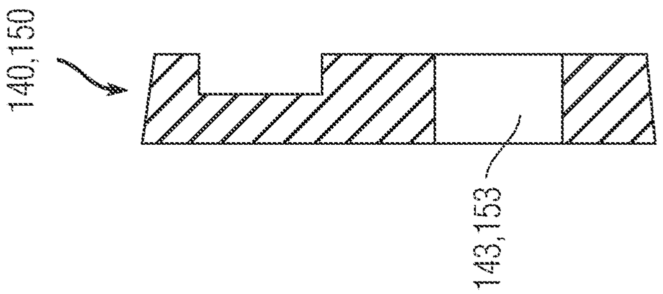
FIG. 8B is a cross-sectional view of the inner support.

FIGS. 1-14 illustrate various components of an upper extremity prosthesis 100 for placement on a residual limb 10 of a person and more particularly, the prosthesis 100 is a below the elbow (transradial) prosthesis. FIG. 10 shows one exemplary prosthesis 100 in a fully assembled state on the residual limb 10. The prosthesis 100 finds particular utility when the patient's residual limb is characterized as being short in length below the elbow (trans ulna) as shown and has an osseointegration post.

In general, the prosthesis 100 (FIGS. 10 and 14) includes inner components and an outer shell as described herein. More specifically, the inner components of the prosthesis provide the means for attaching the prosthesis to the residual limb 10 and also provide the framework for attaching the outer shell.

As mentioned, in one implementation of the prosthesis 100, the prosthesis 100 is used in an osseointegration limb replacement surgical procedure. While FIGS. 1-14 illustrate such an implementation, it will be understood that the prosthesis 100 is not limited to only an osseointegration implementation and can be modified for non-osseointegration implementations.

The inner components of the prosthesis 100 include an elongated member 110 that has a first end 112 and an opposing second end 114. The first end 112 can be considered to be a proximal end and the second end 114 can be considered to be distal end. The elongated member 110 can be in the form of a tube, such as an aluminum tube. The first end 112 is detachably coupled to a first connector 120 and this attachment defines an interface. It is at this interface, that the prosthesis can be removed (detached) such as at night. Additional details concerning this detachment aspect and the interface are described herein. The attachment mechanism between the first end 112 and the first connector 120 is preferably of a type that can be easily disengaged to allow the main part of the prosthesis 100 to be selectively removed (detached), while optionally allowing the first connector 120 to remain in place.

Any number of materials can be used to form the elongated member 110 and in one embodiment, the elongated member 110 can be a metal tube and more preferably, the elongated member 110 is in the form of an aluminum alloy tube.

The first connector 120 has a first face (first/proximal end) 122 and an opposite second face (second/distal end) 124. The first end 112 of the elongated member 110 is coupled to the second face 124 of the first connector 120 in such a way that the first end 112 can be detached and removed from the first connector 120. For example, a quick release type mechanism can be implemented or other type of mechanism that allows for the removal of the elongated member 110.

In one embodiment, the first connector 120 is an adapter that has an adjustable body 123 that can be manipulated so as to clamp the first end 112 of the elongated member 110. The body 123 thus can be a clamp body that includes a slot 125 that partitions the body 123 into two halves. The second face 124 of the first connector 120 includes an opening into which the first end 112 of the elongated member 110 is received. The first connector 120 includes a fastener 129 that is received within the body 123 and serves to: (1) tighten the body 123 about the first end 112 of the elongated member 110 so as to capture the first end 112 and (2) loosen the body 123 about the first end 112 of the elongated member 110. In other words, the tightening of the body 123 causes the two halves of the body 123 to compress and tightening around the first end 112 of the elongated member 110 resulting in a friction fit being formed between the first end 112 and the body 123. In this manner, the elongated member 110 can be held in place. When, such as at night, it is time for the prosthesis to be removed from the residual limb 10, the fastener 129 is loosed to cause the split body 123 to open up allowing for removal of the elongated member 110 from the first connector 120.

It will be appreciated that the first end 112 of the elongated member 110 can be held using other techniques, such as the use of a quick connect. In quick connect mechanisms, the first end 112 would carry a first quick connect part and the second face 124 of the body 123 would carry a second quick connect part that mates with the first quick connect part to attach the two parts. Other techniques can be equally used.

In an osseointegration type implementation, the first connector 120 can be connected to a second connector 130 that comprises an osseointegration post that has a first end 132 that is fixedly attached (implanted) into the ulna (bone) and an opposite second end 134 that is coupled to the first connector 120. The interface and connection between the first connector 120 and the second connector 130 can be of a permanent type in that during the intended use of the prosthesis 100, the connection between the first connector 120 and the second connector 130 is meant to be maintained.

Figure 14:
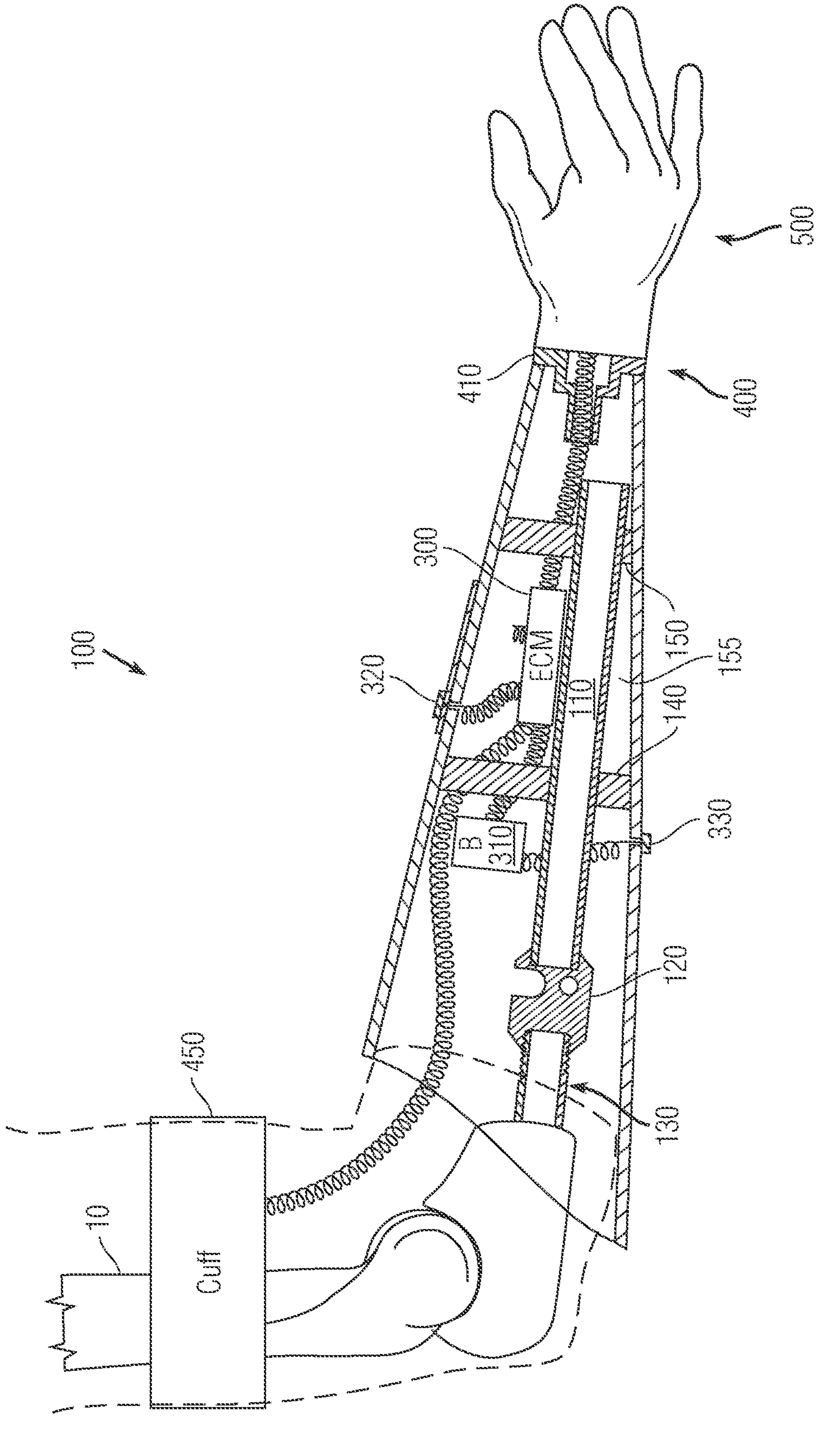
FIG. 14 is a cross-sectional view of the outer prosthetic shell attached to the inner supports and internal electronics along with other accessories are shown.

In one embodiment, the second connector 130 is in the form of an osseointegration dual taper post with outer threads at the exposed second end 134 (e.g., the post can include ½×20 threads). The osseointegration post can thus be a threaded titanium post. The first face of the first connector 120 can include a threaded opening that receives the threaded osseointegration post 130. The osseointegration post 130 is thus anchored into bone (ulna) and provides a support for the first connector 120 (adapter). As shown in FIG. 14, when the elongated member 110 is coupled to the first connector 120 and the second connector 130 is connected to the first connector 120, the elongated member 110 and the second connector 130 are coaxial.

Thus, in the illustrated embodiment, the first and second connectors 120, 130 are intended to be fixedly attached to the bone of the patient, while the main prosthetic components including the forearm structure (shell) is intended to be easily detachable to permit removal as at night or for cleaning, servicing, etc.

It will also be appreciated that the first and second connectors 120, 130 can be combined into a single part that is configured to be implanted into the ulna and mate with the elongated member 110.

The inner components of the prosthesis 100 include a first support 140 and a second support 150 that are configured to provide a framework for attaching an outer prosthetic shell 200 to the inner components. As shown, the outer prosthetic shell 200 can be a forearm shell that surrounds the inner components of the system 100. The outer prosthetic shell 200 has a first end 202 and an opposing second end 204. The first end 202 can be a proximal end and the second end 204 can be a distal end. Like a human arm, the outer prosthetic shell 200 has a tapered construction with the proximal end having a greater width (diameter) than the distal end. As discussed herein, the second end 204 can be thought of as being a wrist end, while the first end 202 is the end closer to the residual limb 10.

In accordance with the present disclosure, the first support 140 and the second support 150 are positioned along the elongated member 110 and are locked in place. In other words, the first support 140 and second support 150 surround and are fixedly attached to the elongated member 110. Each of the first support 140 and the second support 150 can include a main opening 143, 153 which receives the elongated member 110. The elongated member 110 thus passes through the first support 140 and the second support 150; however, during use, the first and second supports 140, 150 are not permitted to freely travel along the length of the elongated member 110.

Each of the first support 140 and the second support 150 can be a disk-shaped (wheel-like) structure that is constructed to surround the elongated member 110 and is configured to mate with the outer prosthetic shell 200. Since the outer prosthetic shell 200 has a tapered construction, a peripheral side wall 142, 152 of the first support 140 and the second support 150, respectively, likewise has a tapered construction since as described herein, this peripheral side wall 142, 152 seats against the inner surface of the tapered outer prosthetic shell 200. In addition, since the first support 140 and the second support 150 are located at different axial locations along the elongated member 110, the widths (diameters) of the first support 140 and the second support 150 are different. More specifically, the first support 140 is located closer to the first end 112 of the elongated member (rod or shaft) 110 compared to the second support 150 and therefore, the first support 140 has a greater diameter (width) compared to the diameter of the second support 150. The distance between the first support 140 and the second support 150 can vary depending upon different parameters like the overall length of the prosthetic shell 200. As a result, a hollow interior space 155 is defined within the outer prosthetic shell 200 between the first support 140 and the second support 150.

As discussed herein, the first support 140 and the second support 150 provide support for the prosthetic shell 200 by providing anchoring points for attaching the prosthetic shell 200 to the two supports. For example, fasteners 170 can be used to couple the prosthetic shell 200 to the first support 140 and the second support 150. More particularly, one or more and preferably a plurality of fasteners 170 can be used to attach the prosthetic shell 200 to the first support 140 and the second support 150. The fasteners 170 can be in the form of screws or the like that pass through the outer prosthetic shell 200 and into one of the first support 140 and the second support 150. The outer prosthetic shell 200 can include through holes that are aligned with the first support 140 and the second support 150 to allow the fasteners to more easily be aligned with and engage the first support 140 and the second support 150.

Threaded holes (bores) in the first support 140 and the second support 150 can be provided to receive the fasteners 170 for attaching the outer prosthetic shell 200 to the first support 140 and second support 150. By way of the first support 140 and the second support 150, the outer prosthetic shell 200 can be attached to the elongated member 110.

As best shown in the cross-sectional view of FIG. 14, each of the first support 140 and the second support 150 is configured to not only accommodate the elongated member 110 but also accommodate electronics that are often times disposed internally within the outer prosthetic shell 200. The first support 140 includes a first opening 143 (first through hole) and similarly, the second support 150 includes a first opening 153 (second through hole). Each of the first openings 143, 153 is designed to receive the elongated member 110 and in particular, the elongated member 110 passes through the first openings 143, 153. The first openings 143, 153 are formed off center (eccentric) in part due to the inwardly tapered construction of the outer prosthetic shell 200. The cross-section of the first openings 143, 153 have complementary shapes to the cross-sectional shape of the elongated member 110 and therefore, the first openings 143, 153 can have a circular cross-section when the elongated member 110 is a circular rod.

Figure 11A:
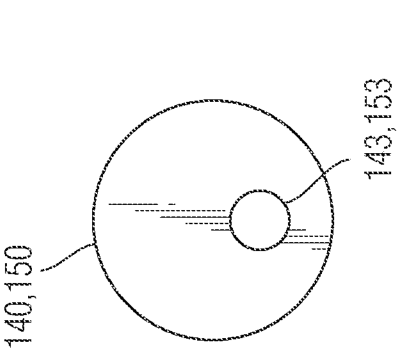
FIG. 11A is a front elevation view of one exemplary inner support.
Figure 11B:
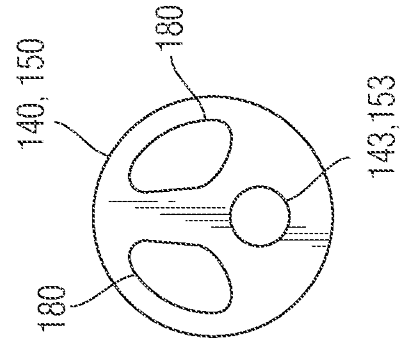
FIG. 11B is a front elevation view of another exemplary inner support.
Figure 11C:
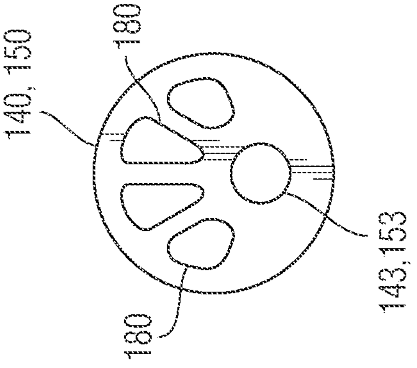
FIG. 11C is a front elevation view of another exemplary inner support.

As can be seen in the cross-sectional view of FIGS. 11A-11C, each of the first support 140 and the second support 150 can include at least one secondary opening or window 180. FIG. 11B illustrates a pair of secondary openings 180 and FIG. 11C shows four secondary openings 180. The pair of secondary openings 180 can also be located off center as shown. These secondary openings 180 are intended to allow passage of objects through the hollow interior of the prosthetic shell 200. For example, electronics that can be located within the prosthetic shell 200 have wires and the like that need to be routed through the hollow interior of the prosthetic shell 200 and thus, need to be routed through the first support 140 and the second support 150. These secondary openings 180 can thus allow wires or even objects to be routed axially within the prosthetic shell 200. It will be appreciated that the secondary openings 180 can have a different shape and/or different size that the corresponding first openings 143, 153. In addition, the secondary openings 180 can have different sizes and/or different shapes.

The profile of the first support 140 and the second support 150 can also be customized as shown in FIGS. 12A-12C and 14. For example, the peripheral side wall of the first support 140 and the second support 150 can be thinned so as to reduce the overall weight of the first support 140 and second support 150. For example, one or more notches 195 can be formed in the peripheral side wall as shown in FIG. 13. The functionality of the notch 195 is described herein.

Figure 12A:
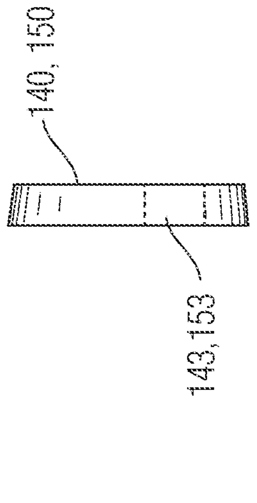
FIG. 12A is a side elevation view of one exemplary inner support.
Figure 12B:
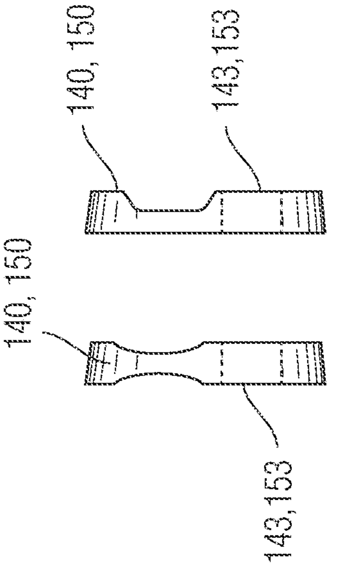
FIG. 12B is a side elevation view of another exemplary inner support.
Figure 12C:
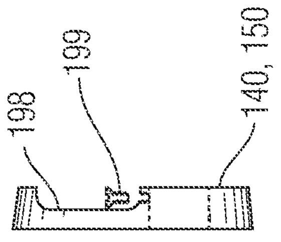
FIG. 12C is a side elevation view of another exemplary inner support.
Figure 13:
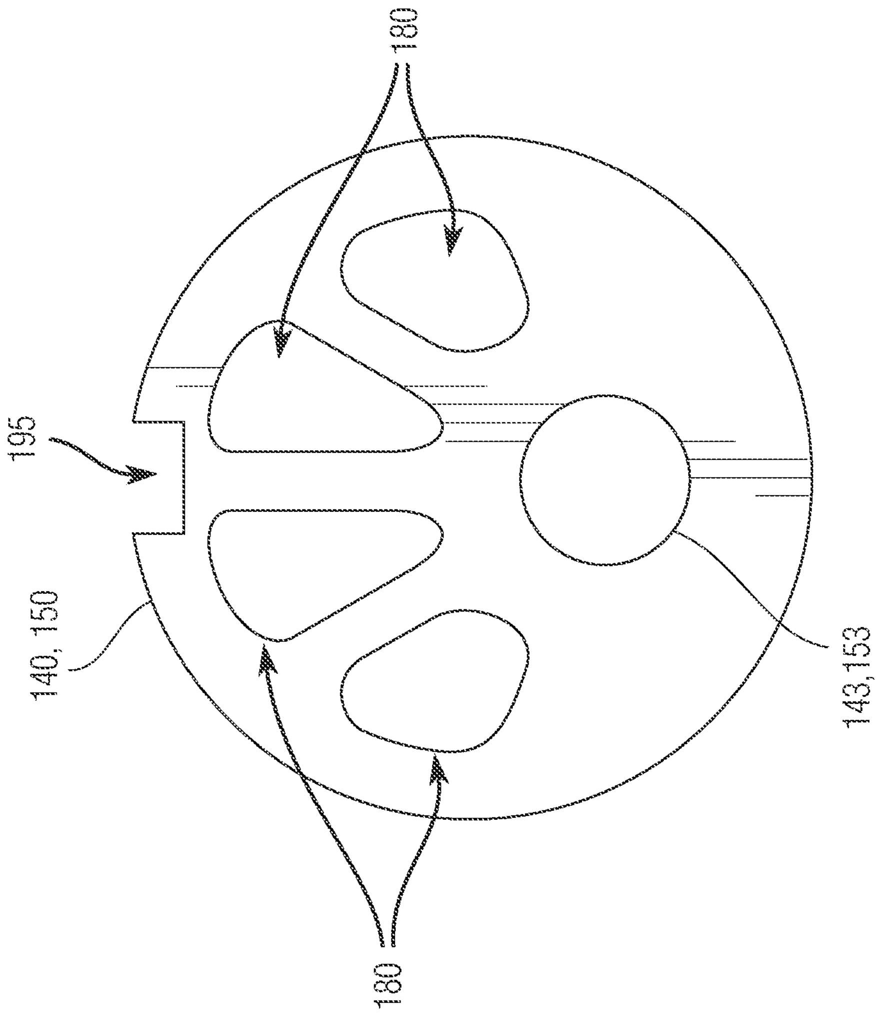
FIG. 13 is a front elevation view of another exemplary inner support with a notch formed on the peripheral side wall.

FIGS. 12A-12C are side elevation views that show the various contours of the inner supports 140, 150. FIG. 12A shows the inner support 140, 150 having a solid construction with beveled peripheral side wall and the opening 143, 153 formed therethrough. FIG. 12B shows an alternative profile in which the body of the inner support 140, 150 is beveled or thinned out on sides to make the body lighter. As shown in FIG. 12C, the body of the inner support 140, 150 can include a notch or recessed portion 198 that has a through hole or the like that communicates with the first opening 143, 153 to allow a fastener 199 to pass into the first opening 143, 153 and into engagement with the elongated member 110. The fastener 199 can be a set screw that is tightened into contact with the elongated member 110 for fixedly attaching the first or second support 140, 150 to the elongated member 110.

As mentioned herein, the first and second supports 140, 150 are fixedly attached to the elongated member 110 such that the supports 140, 150 do not rotate and do not move axially along the elongated member 110. However, the first and second supports 140, 150 are fixedly attached to the outer prosthetic shell 200 and the elongated member 110.

Thus, the first and second supports 140, 150 are multipurpose objects that are multi-functional and not only support and provide attachment points and also allow for the passage and routing of other internal objects as described herein.

Optional Features

The system 100 can also include optional functionality in the form of optional components that can be used with the system 100. These components can include electronics and a power source for powering the electronics. As described herein, the incorporation of electronics necessitates the use of a user interface to allow user control over the electronics. For example, as illustrated in FIG. 14, the electronics can include a main controller 300, such as an electronic control module. The main controller 300 is fixedly attached to the elongated member 110 and thus lies within the outer prosthetic shell 200. The main controller 300 is electrically connected to a power source 310 which can be in the form of a battery pack or the like. The power source 310 is also located within the outer prosthetic shell 200 and is also fixedly connected to the elongated member 110. As shown, a wire or the like can be connected between the power source 310 and the main controller 300.

An actuator 320 is provided to allow the user to control operation of the main controller 300. The actuator 320 can be in the form of a switch or button that is provided along the outer surface of the outer prosthetic shell 200. The actuator 320 can be connected to the main controller 300 by a wire.

A recharging port 330 can be provided along the outer prosthetic shell 200 and is electrically connected to the power source 310. The recharging port 330 can be connected to the power source 310 using a wire or the like. As illustrated, the recharging port 330 is located closer to the power source 310 compared to the main controller 300. The recharging port 330 can be located on one side of the outer prosthetic shell 200 while the actuator 320 can be located on another side of the outer prosthetic shell 200. The recharging port 330 can be any number of types of ports that permit a direct charging of the battery 310. For example, it can be a traditional male plug or it can be any of the commercially available USB type connections or any other suitable connection.

Additional automated components can be included such as a powered wrist 400 that is electrically connected to the main controller 300 and can comprise any number of suitable commercially available products. The powered wrist 400 is thus for placement at the distal end of the outer prosthetic shell 200 and a prosthetic hand 500 can also be provided and coupled to the wrist 400.

As best shown in FIGS. 5A-B and 6A-C, the powered wrist 400 is coupled to the outer prosthetic shell 200 using a wrist coupling member 410 in the form of a wrist unit lamination ring that is configured to mount to the outer prosthetic shell 200 and is configured to allow the powered wrist 400 to be mounted thereto. As illustrated, the wrist coupling member 410 is at the second end 204 of the outer prosthetic shell 200 and is at least partially disposed within the outer prosthetic shell 200. One end of the wrist coupling member 410 is exposed external to the second end 204.

The main controller 300 can also be thought of as being an electronic control module (ECM). The ECM is intended to be electrically connected, via a wire, to the wrist and hand to permit power and control over these components.

As discussed herein, the first support 140 and the second support 150 are each configured in view of the electronics that are contained within the outer prosthetic shell 200. In particular, the first support 140 and the second support 150 allow for the routing of wires and the like in an axial direction internally within the outer prosthetic shell 200. This functionality can be accomplished using the secondary openings 180 and the notch 195 also accommodates the functionality of the device by accommodating the actuator and its operation.

FIG. 14 also illustrates a cuff 450 that is electrically connected to the ECM (main controller 300) via a wire. As is known, the cuff 450 can include electrodes or the like that are mounted on the inside. As shown, the cuff 450 is intended for placement around the residual limb.

Figure 9A:
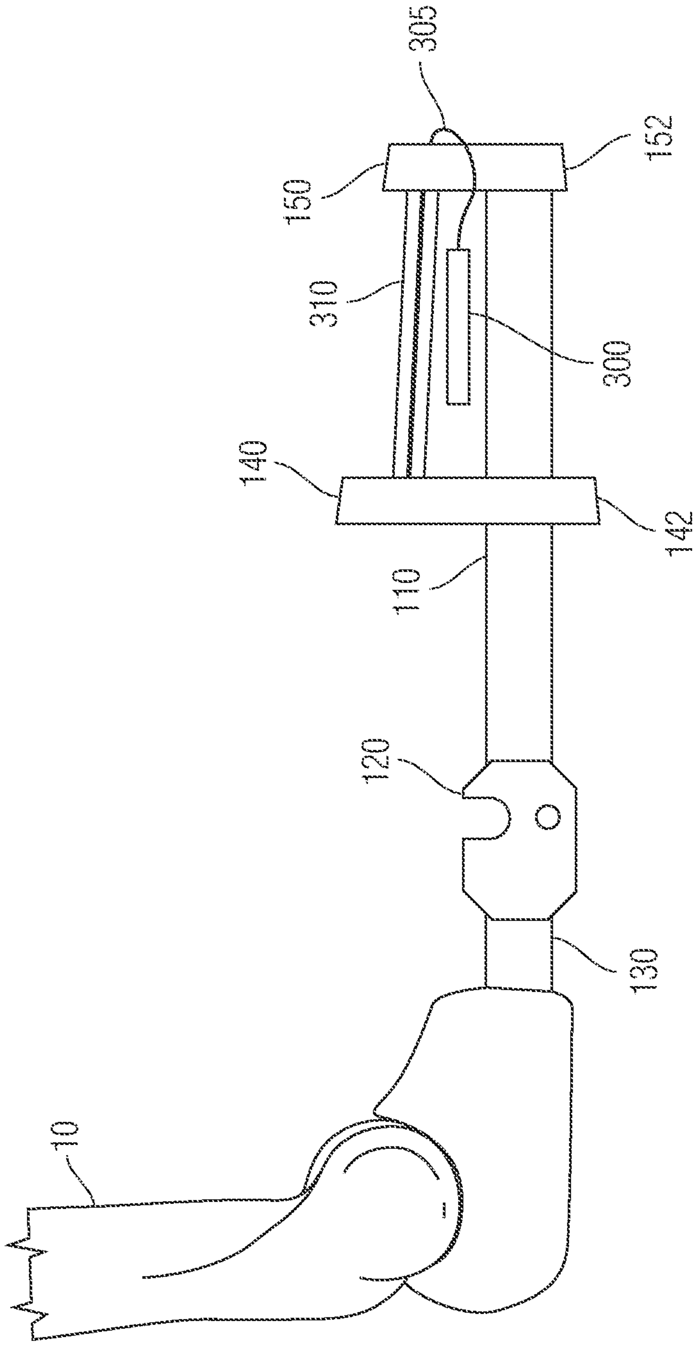
FIG. 9A is a side elevation view of the inner components mounted to the residual limb with a pair of inner supports coupled to the elongated member.
Figure 9B:
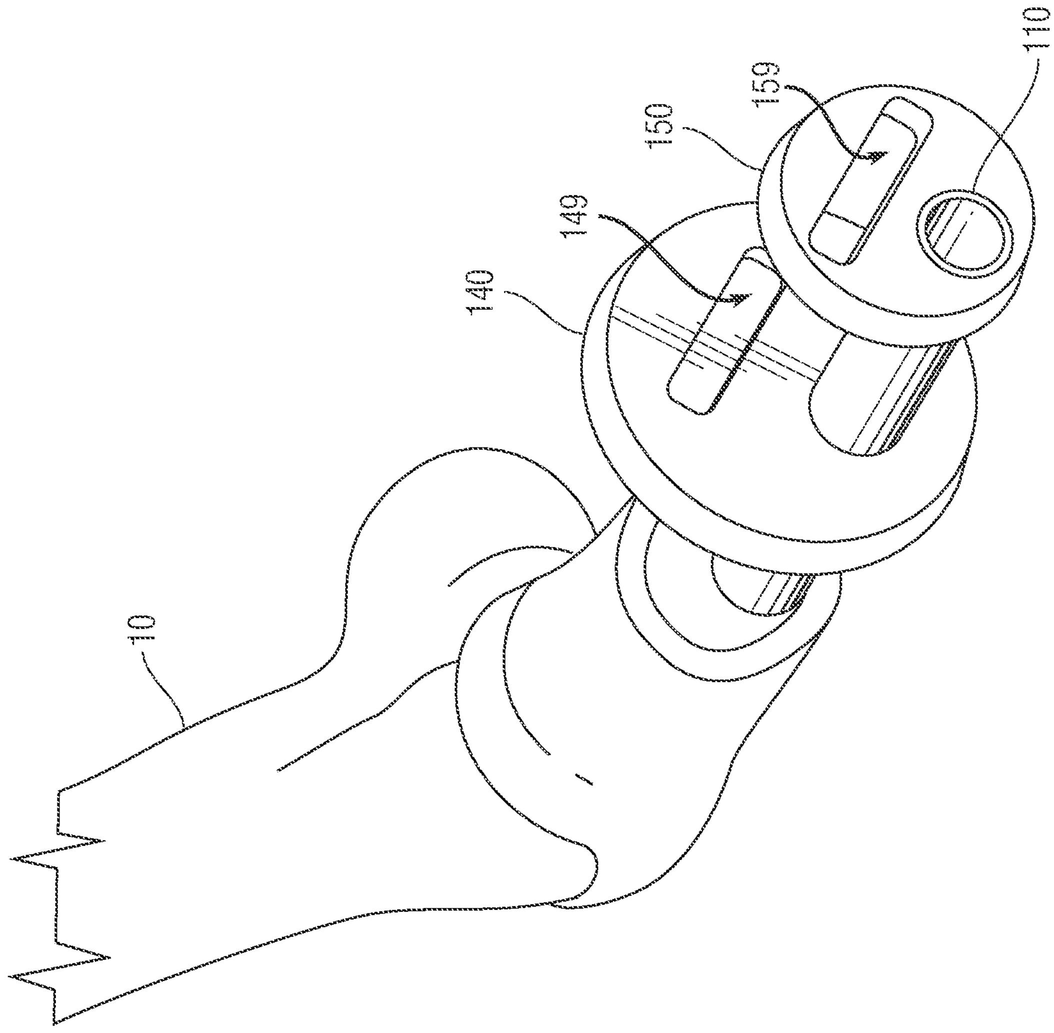
FIG. 9B is an end perspective view showing the inner components.
Figure 10:
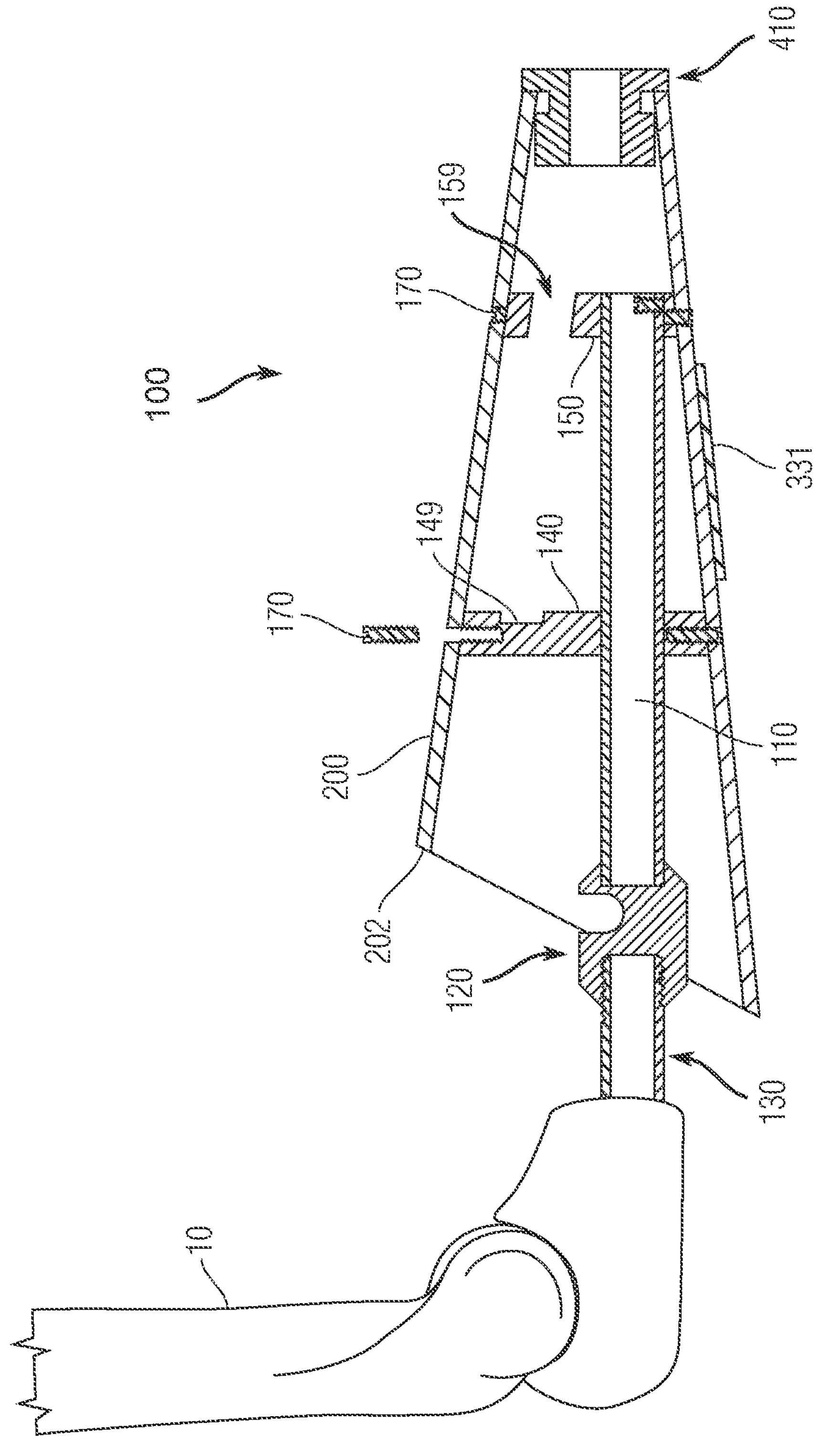
FIG. 10 is a side elevation view of the outer prosthetic shell being coupled to the pair of inner supports using fasteners according to one exemplary embodiment.

FIGS. 9A, 9B and 10 illustrate one exemplary embodiment in which the battery 310 is in the form of a pack that is nested within and held by the first support 140 and the second support 150. The first support 140 includes a recessed portion 149 that is configured (sized and shaped) to receive one end of the battery 310 and more particularly, this end of the battery 310 can be frictionally held within the recessed portion 149 (due to a snug fit). The second support 150 includes a complementary through hole 159. The through hole 159 is sized and shaped to allow the battery 310 to pass through therethrough. The through hole 159 thus serves two purposes, namely, a first purpose is to allow the battery 310 to pass through the second support 150 into the open space between the two supports 140, 150 and the second purpose is to hold and retain one end of the battery 310 (while the other end lies within the recessed portion 149). The through hole 159 is also aligned relative to the recessed portion 149 to allow the battery 310 to pass through the through hole 159 and then into the recessed portion 149. The through hole 159 and recessed portion 149 thus are designed in view of the size and shape of the battery 310 and provided a means for receiving and holding the battery 310 between the first and second supports 140, 150. By sizing the recessed portion 149 and through hole 159 in view of the footprint of the battery 310, the battery 310 can be securely held in place between the shell 200 and the elongated member 110. As shown in FIGS. 9B and 10, the distal end of the elongated member 110 can be terminated at the second support 150 in that the elongated member 110 does not extend distally beyond the second support 150 (but instead is flush thereto). FIG. 9A shows the location of the main controller 300 below the battery 310 and above the elongated member 110. The main controller 300 is attached to the battery 310 via one or more wires 305 and it is this connection that provides the means for holding the main controller 300 in place. In other words, there main controller 300 is suspended in the space between the elongated member 110 and the battery 310. In the illustrated embodiment, the main controller 300 is not directly and fixedly attached to the elongated member 110 and the battery 310. The length of the wire 305 prevents the main controller 300 from excessively moving.

To load the battery 310, the battery 310 is slid through the through hole 159 and is delivered into the recessed portion 149.

It will be appreciated that the locations of the recessed portion 149 and through hole 159 can be reversed in that the recessed portion 149 can be formed in the second support 150 and the through hole 159 can be formed in the first support 140.

FIG. 10 illustrates one manner, which was previously described with reference to other embodiments, of attaching the first and second supports 140, 150 to the elongated member 110 and for attaching the first and second supports 140, 150 to the shell itself. As mentioned, in one embodiment, a screw can be used to attach each of the first and second supports 140, 150 to the elongated member 110 and as shown, can at least partially extend into the hollow interior of the elongated member 110.

Figure 15:
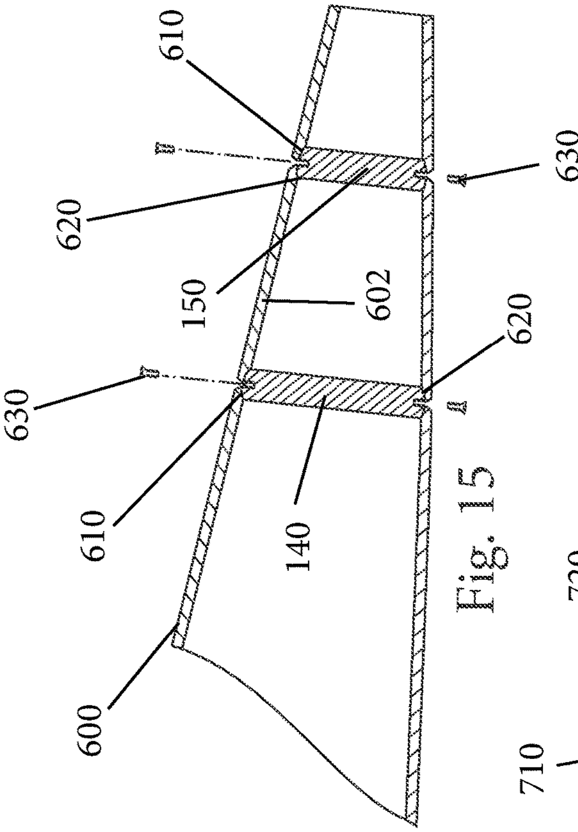
FIG. 15 is a cross-sectional view of an outer prosthetic shell according to another embodiment.

FIG. 15 is a cross-sectional view of an outer prosthetic shell 600 defined by an inner surface 602. The inner surface 602 includes at least one first coupling element 610 that is configured to mate with a second coupling element 620 that is part of one of the first support 140 and second support 150. For example, the first coupling element 610 can be in the form of a recess formed along the inner surface 602 and more particularly, the recess can have a concave shape. When the first coupling element 610 is in the form of a concave shaped recess, the second coupling element 620 can be in the form of complementary outer peripheral edge of the first support 140 or the second support 150. For example, the outer peripheral edge can be in the form of a convex edge that is configured to be received into the concave shaped recess in a locking manner. In other words, the inner surface 602 can have two concave shaped recesses that are spaced apart along the inner surface 602. The first and second supports 140, 150 are sized so that they interlockingly engage the recesses when the outer peripheral edge of the respective first support 140, 150 is aligned with and engages the recess. Since the inner surface 602 is tapered, the first and second supports 140, 150 are sized such that second support 150 is inserted first into the wider open end of the shell and is then moved forward therein until the outer peripheral edge of the second support 150 contacts the inner surface 602 immediately before the concave shaped recess and then further forward movement of the second support 150 causes slight flexing of the outer shell 400 to allow reception of the convex outer peripheral edge into the concave shaped recess (first coupling element 610). In other words, the second support 150 snap-lockingly mates with the concave shaped recess that is closer to the distal end of the shell. Similarly, the first support 140 is inserted subsequently into the wider open end of the shell 400 and is then moved forward therein until the outer peripheral edge of the second support 150 contacts the inner surface 602 immediately before the concave shaped recess and then further forward movement of the first support 140 causes slight flexing of the outer shell 400 to allow reception of the convex outer peripheral edge into the other concave shaped recess (first coupling element 610). In other words, the first support 140 snap-lockingly mates with the concave shaped recess that is closer to the proximal end of the shell. Fasteners 630 can be used to secure the first and second supports 140, 150 to the shell 400. The fasteners 630 can be in the form of screws that pass through the shell 400 into the concave shaped recesses and into the peripheral outer edges of the first and second supports 140, 150.

While FIG. 15 shows the first coupling elements 610 is in the form of concave shaped recesses and the second coupling elements 620 are in the form of convex shaped outer edges of the supports 140, 150, the opposite can equally be true in that the first coupling elements 610 can be convex shaped bumps formed along the inner surface 602 and the second coupling elements 620 can be in the form of a concave shaped groove or recess formed in the outer peripheral edge of the supports 140, 150.

Figure 16:
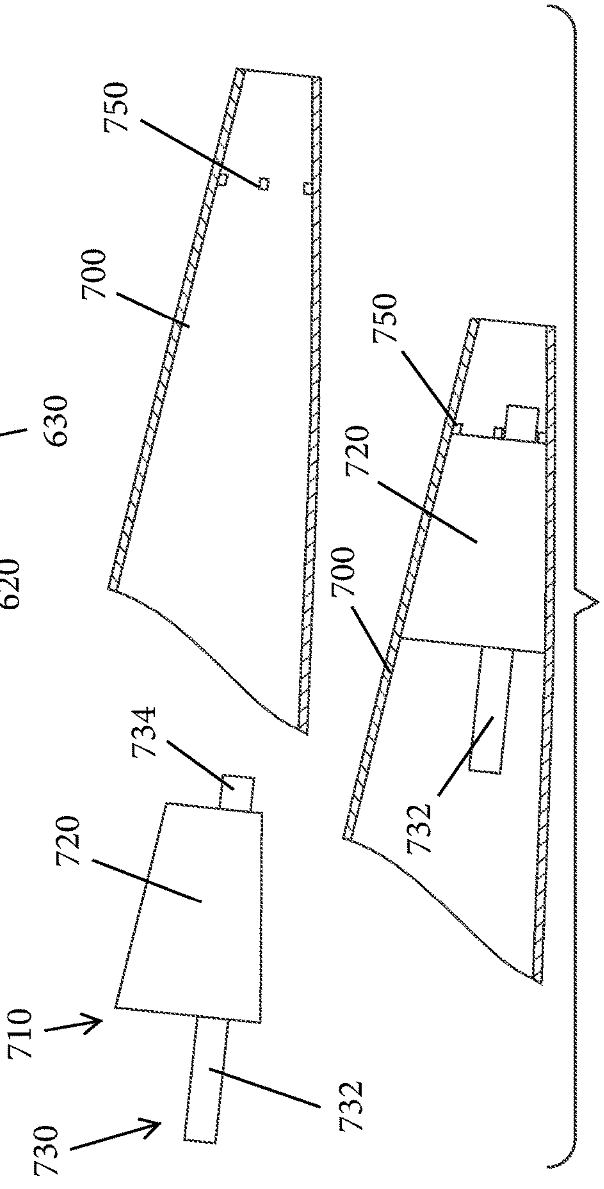
FIG. 16 is an exploded, partial cross-sectional view of an outer prosthetic shell according to another embodiment.

FIG. 16 is an exploded cross-sectional view of an outer prosthetic shell 700 that can be the same or similar to the outer prosthetic shell 200. In this embodiment, the elongated member 110 and the first and second supports 140, 150 are eliminated and replaced by an insert 710. The inner surface of the outer prosthetic shell 700 is tapered as in the case of shell 200. The insert 710 has a block portion 720 and one or more elongated members 730. The block portion 720 is likewise tapered in a complementary manner to the inner surface of the shell 700. Thus, the block portion 720 can be inserted into the open proximal end of the shell 700, the block portion 720 can freely move in a distal direction. As the insert 710 moves toward the narrower distal end of the shell 700, the tapered outer surface of the insert 710 contacts the tapered inner surface of the shell 700 and the insert 710 in effect becomes wedged within the hollow interior of the shell 700 at the desired target location. The insert 710 is thus flush with the inner surface of the shell 700.

In addition, the shell 700 can optionally include one or more stops 750 that are formed along the inner surface of the shell 700 and serve to restrict and prevent distal movement of the insert 710 within the shell 700.

In FIG. 16, the elongated member 730 can include a first section 732 at the proximal end of the block portion 720 and a second section 734 at the distal end of the block portion 720. The length of the first section 732 is greater than a length of the second section 734. As in the previous embodiments, the first section 732 is designed to mate with the first connector 120 and the second section 734 mates with the wrist unit. Fasteners, as previously discussed, can be used to attach the block portion 720 to the shell 700.

In this embodiment, the insert 710 is a single part that can be easily inserted into the hollow interior of the shell 700 and then moved to the correct target position therein where is it secured in placed as by using fasteners or other techniques.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. An upper extremity prosthesis for placement on a residual limb of a person comprising:

an elongated member having a first end and an opposite second end;

an outer prosthetic shell having a first end and an opposite second end; and at least a first support and a second support, wherein the first support and the second support surround and are fixedly coupled to the elongated member at first and second attachment points, respectively, the outer prosthetic shell surrounding and being coupled to the first support and the second support;

wherein an inner face of the first support includes a recessed section and the second support includes a through hole that is colinear with the recessed section.

2. The upper extremity prosthesis of claim 1, wherein each of the first support and the second support comprises a circular body with a through hole for receiving the elongated member.

3. The upper extremity prosthesis of claim 2, wherein the through hole is formed off-center and a peripheral side wall of the circular body has a tapered construction.

4. The upper extremity prosthesis of claim 2, wherein the first support has a first diameter that is greater than a second diameter of the second support.

5. The upper extremity prosthesis of claim 1, wherein each of the first support and the second support comprises a body with a through hole for receiving the elongated member and has at least one window or opening formed therein for allowing passage of an object.

6. The upper extremity prosthesis of claim 5, wherein the object comprises one or more wires.

7. The upper extremity prosthesis of claim 5, wherein the through hole is formed off center and the at least one window is formed off center.

8. The upper extremity prosthesis of claim 5, wherein an outer peripheral wall of the body includes a notch.

9. The upper extremity prosthesis of claim 8, further comprising electronics, wherein the electronics include an electronic control module (ECM) with a switch that is accommodated within the notch.

10. The upper extremity prosthesis of claim 1, wherein each of the first support and the second support comprises a body with a through hole for receiving the elongated member, the body having a notch formed therein with a fastener extending through the body and into communication with the through hole for contacting the elongated member to fixedly attach the body to the elongated member.

11. The upper extremity prosthesis of claim 1, further including a plurality of fasteners for fixedly attaching the outer prosthetic shell to the first support and the second support.

12. The upper extremity prosthesis of claim 11, wherein the plurality of fasteners are anchored into the first support and the second support.

13. The upper extremity prosthesis of claim 1, wherein a first end portion of a battery pack is received within the recessed section and an opposite second end portion of the battery pack is disposed within the through hole.

14. The upper extremity prosthesis of claim 13, wherein the battery pack is held by friction fit within the recessed section and the through hole.

* * * * *